United States Patent
Pyun et al.

(10) Patent No.: US 10,920,020 B2
(45) Date of Patent: Feb. 16, 2021

(54) 3D-PRINTING OF ULTRA-HIGH REFRACTIVE INDEX POLYMERS

(71) Applicant: ARIZONA BOARD OF REGENTS ON BEHALF OF THE UNIVERSITY OF ARIZONA, Tucson, AZ (US)

(72) Inventors: Dong-Chul Pyun, Tucson, AZ (US); Rongguang Liang, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 405 days.

(21) Appl. No.: 15/857,273

(22) Filed: Dec. 28, 2017

(65) Prior Publication Data

US 2018/0105649 A1 Apr. 19, 2018

Related U.S. Application Data

(63) Continuation-in-part of application No. PCT/US2016/042057, filed on Jul. 13, 2016, and a
(Continued)

(51) Int. Cl.
*B33Y 10/00* (2015.01)
*C08G 75/16* (2006.01)
(Continued)

(52) U.S. Cl.
CPC .............. *C08G 75/16* (2013.01); *A01N 41/12* (2013.01); *A01N 59/02* (2013.01); *A61K 31/795* (2013.01);
(Continued)

(58) Field of Classification Search
CPC .. A61K 31/795; B29C 64/106; B29C 64/124; B29C 64/165; B33Y 10/00; C08G 75/14; C08J 2381/04; C08L 81/04
See application file for complete search history.

(56) References Cited

U.S. PATENT DOCUMENTS

| 2,779,761 A | 1/1957 | Kibler |
| 2,989,513 A | 6/1961 | Hendry et al. |

(Continued)

FOREIGN PATENT DOCUMENTS

| CN | 104713968 A1 | 6/2015 |
| EP | 0806451 A1 | 11/1997 |

(Continued)

OTHER PUBLICATIONS

Chung, W.J. et al., "Elemental Sulfur as a Reactive Medium for Gold Nanoparticles and Nanocomposite Materials", Angewandte Chemie International Edition, 2011, 50, 11409-11412.
(Continued)

*Primary Examiner* — Michael A Salvitti
(74) *Attorney, Agent, or Firm* — Nguyen Tarbet LLC (57) ABSTRACT

Sulfur copolymers having high sulfur content for use as raw materials in 3D printing. The sulfur copolymers are prepared by melting and copolymerizing one or more comonomers with cyclic selenium sulfide, elemental sulfur, elemental selenium, or a combination thereof. Optical substrates, such as films and lenses, are constructed from the sulfur copolymer via 3D printing and are substantially transparent in the visible and infrared spectrum. The optical substrates can have refractive indices of about 1.75-2.6 at a wavelength in a range of about 500 nm to about 8 μm.

20 Claims, 5 Drawing Sheets

Related U.S. Application Data continuation-in-part of application No. 15/287,118, filed on Oct. 6, 2016, now Pat. No. 10,833,330, which is a continuation of application No. 14/622,429, filed on Feb. 13, 2015, now Pat. No. 9,567,439, which is a continuation-in-part of application No. 14/237,659, filed as application No. PCT/US2012/050602 on Aug. 13, 2012, now Pat. No. 9,306,218.

(60) Provisional application No. 62/440,576, filed on Dec. 30, 2016, provisional application No. 62/191,760, filed on Jul. 13, 2015, provisional application No. 62/203,525, filed on Aug. 11, 2015, provisional application No. 62/210,170, filed on Aug. 26, 2015, provisional application No. 62/212,188, filed on Aug. 31, 2015, provisional application No. 62/306,865, filed on Mar. 11, 2016, provisional application No. 62/313,010, filed on Mar. 24, 2016, provisional application No. 62/329,402, filed on Apr. 29, 2016, provisional application No. 62/039,561, filed on Aug. 20, 2014, provisional application No. 62/039,588, filed on Aug. 20, 2014, provisional application No. 62/017,750, filed on Jun. 26, 2014, provisional application No. 61/940,102, filed on Feb. 14, 2014, provisional application No. 61/685,847, filed on Mar. 26, 2012, provisional application No. 61/574,957, filed on Aug. 12, 2011, provisional application No. 61/574,903, filed on Aug. 11, 2011.

(51) Int. Cl.
| | |
|---|---|
| H01M 4/60 | (2006.01) |
| C01B 17/96 | (2006.01) |
| C08L 81/04 | (2006.01) |
| C08J 3/28 | (2006.01) |
| A61K 31/795 | (2006.01) |
| C01B 3/04 | (2006.01) |
| A01N 59/02 | (2006.01) |
| A01N 41/12 | (2006.01) |
| B29C 64/106 | (2017.01) |
| B29C 64/165 | (2017.01) |
| B29C 64/124 | (2017.01) |
| B33Y 70/00 | (2020.01) |
| H01M 4/38 | (2006.01) |
| H01M 10/052 | (2010.01) |
| C08G 75/14 | (2006.01) |

(52) U.S. Cl.
CPC .......... *B29C 64/106* (2017.08); *B29C 64/124* (2017.08); *B29C 64/165* (2017.08); *B33Y 10/00* (2014.12); *B33Y 70/00* (2014.12); *C01B 3/042* (2013.01); *C01B 17/96* (2013.01); *C08J 3/28* (2013.01); *C08L 81/04* (2013.01); *H01M 4/606* (2013.01); *C08G 75/14* (2013.01); *C08J 2381/04* (2013.01); *C08L 2201/52* (2013.01); *H01M 4/382* (2013.01); *H01M 10/052* (2013.01)

(56) References Cited

U.S. PATENT DOCUMENTS

| | | | |
|---|---|---|---|
| 3,251,797 A | 5/1966 | De Pugh et al. | |
| 3,290,266 A | 12/1966 | Barnes et al. | |
| 3,542,701 A | 11/1970 | van Raamsdonk | |
| 3,563,962 A | 2/1971 | Mirviss | |
| 3,767,613 A | 10/1973 | Dix et al. | |
| 3,892,686 A | 7/1975 | Woo | |
| 4,000,347 A | 12/1976 | Ranney et al. | |
| 4,094,751 A | 6/1978 | Nozik | |
| 4,238,585 A | 12/1980 | Bertozzi | |
| 4,346,191 A | 8/1982 | Blount | |
| 4,382,846 A | 5/1983 | Gratzel et al. | |
| 4,568,435 A | 2/1986 | Shelnutt | |
| 4,606,798 A | 8/1986 | Sasse et al. | |
| 4,671,896 A | 6/1987 | Hasegawa et al. | |
| 4,749,347 A | 6/1988 | Valavaara | |
| 4,752,507 A | 6/1988 | Johansson et al. | |
| 4,833,048 A | 5/1989 | DeJonghe et al. | |
| 5,115,060 A | 5/1992 | Grey | |
| 5,121,329 A | 6/1992 | Crump | |
| 5,279,910 A | 1/1994 | Sasaki et al. | |
| 5,371,176 A | 6/1994 | Bezwada et al. | |
| 5,362,493 A | 11/1994 | Skotheim et al. | |
| 5,811,470 A | 9/1998 | Prindle et al. | |
| 5,929,202 A | 7/1999 | Arita et al. | |
| 6,011,094 A | 1/2000 | Planche et al. | |
| 6,072,026 A | 6/2000 | Kawase et al. | |
| 6,111,030 A | 8/2000 | Hartman et al. | |
| 9,306,218 B2 * | 4/2016 | Pyun .................... | H01M 4/382 |
| 9,463,597 B2 | 10/2016 | Van De Vrie et al. | |
| 9,567,439 B1 * | 2/2017 | Pyun .................... | C01B 3/042 |
| 2001/0047043 A1 | 11/2001 | Okoroafor et al. | |
| 2001/0047403 A1 | 11/2001 | Okoroafor et al. | |
| 2002/0039680 A1 | 4/2002 | Hwang et al. | |
| 2004/0207123 A1 * | 10/2004 | Patel ..................... | B33Y 70/00 |
| | | | 264/401 |
| 2007/0010600 A1 | 1/2007 | Goodman et al. | |
| 2007/0253772 A1 | 11/2007 | Kubo et al. | |
| 2008/0038645 A1 | 2/2008 | Kolosnitsyn et al. | |
| 2010/0029163 A1 | 2/2010 | Ogle et al. | |
| 2011/0245360 A1 | 10/2011 | Hahn et al. | |
| 2011/0263755 A1 | 10/2011 | Mohamed et al. | |
| 2012/0264837 A1 | 10/2012 | Eberstaller et al. | |
| 2013/0040197 A1 | 2/2013 | Liu et al. | |
| 2013/0064904 A1 | 3/2013 | Gojon-Romanillos et al. | |
| 2014/0110881 A1 | 4/2014 | Keledjian et al. | |
| 2014/0199592 A1 * | 7/2014 | Pyun .................... | H01M 4/043 |
| | | | 429/213 |
| 2015/0203638 A1 | 7/2015 | Sivanandan et al. | |
| 2018/0079865 A1 | 3/2018 | Pyun | |
| 2018/0105649 A1 * | 4/2018 | Pyun .................... | A01N 41/12 |
| 2018/0208686 A1 * | 7/2018 | Pyun .................... | C08F 12/08 |
| 2018/0264688 A1 * | 9/2018 | Jaker ................... | B33Y 80/00 |
| 2019/0338076 A1 * | 11/2019 | Pyun .................... | H01M 4/606 |

FOREIGN PATENT DOCUMENTS

| | | |
|---|---|---|
| EP | 1882713 A1 | 1/2008 |
| EP | 2093605 A1 | 8/2009 |
| EP | 2896644 A1 | 7/2015 |
| GB | 1203577 A | 8/1970 |
| GB | 1516554 A | 7/1978 |
| WO | WO1995018652 A1 | 7/1995 |
| WO | WO2007076067 A3 | 7/2007 |
| WO | WO2009158385 A | 12/2009 |
| WO | WO2013023216 A1 | 2/2013 |
| WO | WO2013155038 A1 | 10/2013 |
| WO | WO2014052255 A1 | 4/2014 |
| WO | WO2014179100 A1 | 11/2014 |
| WO | WO2015123552 A1 | 8/2015 |

OTHER PUBLICATIONS

Colquhoun, Howard M., "Materials that heal themselves", Nature Chemistry, Jun. 2012, vol. 4, 435-436.

Yang, Ying and Urban Marek W., "Self-healing polymeric materials", Chem. Soc. Rev., 2013, 42, 7446-7467.

Hasegawa, Urara and Van Der Vlies, André J., "Design and Synthesis of Polymeric Hydrogen Sulfide Donors", Bioconjugate Chemistry, 2014, 25 (7), 1290-1300.

Foster, Jeffrey C., et al., "S-Aroylthiooximes: A Facile Route to Hydrogen Sulfide Releasing Compounds with Structure-Dependent Release Kinetics", Organic Letters. 2014, 16, 1558-1561.

(56) References Cited

OTHER PUBLICATIONS

Wurthner, F., "Perylene bisimide dyes as versatile building blocks for functional supramolecular architectures", Chem. Commun. 2004, 1564-1579.
Chung, W.-. et al., "The use of elemental sulfur as an alternative feedstock for polymeric materials", Nature Chemistry 2013, vol. 5, 518-524.
Simmonds, A.G. et a., "Inverse Vulcanization of Elemental Sulfur to Prepare Polymeric Electrode Materials for Li—S Batteries", ACS Macro Lett. 2014, 3, 229-232.
Liu, G. et al., "α-Sulfur Crystals as a Visible-Light-Active Photocatalyst", J. Am. Chem. Soc. 2012, 134, 9070-9073.
Asmus, K.-D., "Pulse Radiolysis Methodology", Methods in Enzymology 1984, 105, 167-178.
Nishide, et al., "Toward Flexible Batteries", (2008) Science, vol. 319, 737-738.
Nishide, et al., "Emerging N-Type Redox-Active Radical Polymer for a Totally Organic Polymer-Based Rechargeable Battery", (2009), Adv Mater, 21, 1627-1630.
Tarascon, et al., "Key challenges in future Li-battery research", (2010) Phil Trans R Soc A, 368, 3227.
Rotinjanz, et al. (1908) Z. Physik Chem, 62, 609.
Bacon, et al., "The Viscosity of Sulfur", (1943) J Am Chem Soc, 65, 639.
Eyring, et al., "The Properties of Liquid Sulfur", (1943) J Am Chem 65, 648.
Tobolsky, A. V. et al., "Equilibrium Polymerization of Sulfur", Am. Chem. Soc.1959, 81, 780.
Penczek, et al. (1974) Nature, 273, 738.
Nazar et al., "A highly ordered nanostructured carbon-sulphur cathode for lithium-sulphur batteries", Nature Mater. 2009, 8, 500-506.
Scrosati, et al., "A High-Performance Polymer Tin Sulfur Lithium Ion Battery", Angew. Chem. Int. Ed. 2010, 49, 2371-2374.
Chen, et al., J. Phys. Chem. C 2011, 115, 6057-6063.
Yang, et al., ACS Nano 2011, 5, 9187-9193.
Bartlett, et al., (1956) J Am Chem Soc, 78, 3710.
McGrath, et al. (2006) Polymer, 47, 4042.
Ueda et al., (2009) J Mater Chem, 19, 8907.
Trofimov, et al. (2002) "Sulfur-rich copolymers of sulfur with 5-vinylbicyclo hept-2-ene and tricyclo deca-3,8-diene as prospective cathode materials for lithium cells," Sufur Letters, 25: 219-227.
Ning, et al., (2004) "Novel cathode material based on chloropolystyrene," PMSE Preprints, American Chemical Society 90: 396-397.
Wang, et al., Nano Lett. 2011, 11, 2644-2647.
Zheng, et al., Nano Lett. 2011, 11, 4462-4467.
Li, et al., Proc. Nail. Acad. Sci. U.S.A. 2013, 110, 7148-7153.
Zheng, et al., Nano Lett. 2013, 13, 1265-1270.
Zhou, et al., ACS Nano 2013, 7, 8801-8808.
Seh, et al., Nat. Commun. 2013, 4.
Li, et al., Nano Lett. 2013, 13, 5534.
Liu, et al., Nat. Nanolech. 2014, 9, 187.
Pyun, J. Angew. Chem Int. Ed., 2011, 50, 11409-11412.
Woo et al. Nature Chemistry. Jun. 2013. vol. 5, pp. 518-524. Published online Apr. 14, 2013.
Suzuki et al. Hydrogen generation using water-insoluble polymer-bound ruthenium(ii) Complexes. Chemical Communications, 1997, Issue 2, p. 227.
Suzuki et al. Photoinduced hydrogen generation from water-insoluble polymer photosensitizer films. Polymer, 1998, vol. 39, Issue 8, p. 1539-1543.
Suzuki et al. Photoinduced hydrogen generation using polymer photosensitizers. Macromolecular Chemistry and Physics, Jun. 1998, vol. 199, Issue 6.
Wang et al. A metal-free polymeric photocatalyst for hydrogen production from water under visible light. Nature Materials 8, 76-80 (2009).
Goldsmith et al. Discovery and High-Throughput Screening of Heteroleptic Iridium Complexes for Photoinduced Hydrogen Production. J. Am. Chem. Soc., 2005, 127 (20), pp. 7502-7510.
Tinker et al. Visible Light Induced Catalytic Water Reduction without an Electron Relay. Chemistry—A European Journal, 2007, vol. 13, Issue 31, pp. 8726-8732.
Happ et al. Towards Hydrogen Evolution Initiated by LED Light: 2-(1 H-1,2,3-Triazol-4-yl)pyridine containing Polymers as Photocatalyst. Macromolecular Rapid Communications, Apr. 2015, vol. 36, Issue 7, 671-677.
Aguirre De Carcer et al. Active-Site Models for Iron Hydrogenases: Reduction Chemistry of Dinuclear Iron Complexes. Inorg. Chem., 2006, 45 (20), pp. 8000-8002.
Alongia et al. Caseins and hydrophobins as novel green flame retardants for cotton fabrics. Polymer Degradation and Stability vol. 99, Jan. 2014, pp. 111-117.
Beom-Young Ryu and Todd Emrick. Thermally Induced Structural Transformation of Bisphenol-1,2,3-triazole Polymers: Smart, Self-Extinguishing Materials. Angew. Chem. Int. Ed. 2010, 49, 9644-9647.
Laufer et al. Clay-Chitosan Nanobrick Walls: Completely Renewable Gas Barrier and Flame-Retardant Nanocoatings. ACS Appl. Mater Interfaces 2012, 4, 1643-1649.
Laufer et al. Exceptionally Flame Retardant Sulfur-Based Multilayer Nanocoating for Polyurethane Prepared from Aqueous Polyelectrolyte Solutions. ACS Macro Lett., 2013, 2 (5), pp. 361-365.
Li et al. Intumescent All-Polymer Multilayer Nanocoating Capable of Extinguishing Flame on Fabric. Adv. Mater. 2011, 23, 3926-3931.
Ding et al. Photoelectrocatalytic Water Splitting: Significance of Cocatalysts, Electrolyte, and Interfaces. ACS Catal. 2017, 7, 675-688.
Swenson, M. Synthesis and Characterization of [Fe Fe) Hydrogenase Mimics. The University of Arizona, 2013, pp. 1-157 online), [retrieved on Jan. 19, 2018). Retrieved from the Internet <http://arizona.openrepository.com/arizona/handle/1 0150/294029>.

\* cited by examiner

Composition:
35 wt% $S_8$
35 wt% $Se_nS_m$
30 wt% DIB

3D-PRINTING OF ULTRA-HIGH REFRACTIVE INDEX POLYMERS

CROSS REFERENCE

This application is a non-provisional and claims benefit of U.S. Provisional Application No. 62/440,576 filed Dec. 30, 2016, the specification(s) of which is/are incorporated herein in their entirety by reference.

Also, this application is a continuation-in-part and claims benefit of PCT Application No. PCT/US16/42057 filed Jul. 13, 2016, which claims benefit of U.S. Provisional Application No. 62/191,760 filed Jul. 13, 2015, U.S. Provisional Application No. 62/203,525 filed Aug. 11, 2015, U.S. Provisional Application No. 62/210,170 filed Aug. 26, 2015, U.S. Provisional Application No. 62/212,188 filed Aug. 31, 2015, U.S. Provisional Application No. 62/306,865 filed Mar. 11, 2016, U.S. Provisional Application No. 62/313,010 filed Mar. 24, 2016, and U.S. Provisional Application No. 62/329,402 filed Apr. 29, 2016, the specification(s) of which is/are incorporated herein in their entirety by reference.

Also, this application is a continuation-in-part and claims benefit of U.S. patent application Ser. No. 15/287,118 filed Oct. 6, 2016, which is a continuation and claims benefit of U.S. patent application Ser. No. 14/622,429 filed Feb. 13, 2015, now U.S. Pat. No. 9,567,439, which claims priority to U.S. Provisional Application No. 62/039,561 filed Aug. 20, 2014, U.S. Provisional Application No. 62/039,588 filed Aug. 20, 2014, U.S. Provisional Application No. 62/017,750 filed Jun. 26, 2014, and U.S. Provisional Application No. 61/940,102 filed Feb. 14, 2014, the specification(s) of which is/are incorporated herein in their entirety by reference.

Furthermore, U.S. patent application Ser. No. 14/622,429, now U.S. Pat. No. 9,567,439, is a continuation-in-part and claims benefit of U.S. patent application Ser. No. 14/237,659 filed Mar. 11, 2014, now U.S. Pat. No. 9,306,218, which is a 371 of PCT Application No. PCT/US12/50602 filed Aug. 13, 2012, which claims benefit of U.S. Provisional Application No. 61/685,847 filed Mar. 26, 2012, U.S. Provisional Application No. 61/574,957 filed Aug. 12, 2011, and U.S. Provisional Application No. 61/574,903 filed Aug. 11, 2011, the specification(s) of which is/are incorporated herein in their entirety by reference.

FIELD OF THE INVENTION

The present invention relates to the fabrication of optical components and devices via 3D-printing of ultra-high refractive index copolymers prepared from sulfur-, selenium-, and chalcogenide-containing monomers and organic comonomers.

BACKGROUND OF THE INVENTION

An incredible abundance of elemental sulfur ($S_8$), nearly 7-million tons is generated as a waste byproduct from hydrodesulfurization of crude petroleum feedstocks, which converts alkanethiols and other (organo) sulfur compounds into $S_8$. Current industrial utilization of elemental sulfur is centered around sulfuric acid, agrochemicals, and vulcanization of rubber. For example, elemental sulfur is used primarily for sulfuric acid and ammonium phosphate fertilizers, where the rest of the excess sulfur is stored as megaton-sized, above ground sulfur towers. Hence, there is a need for the production of new materials that offers significant environmental and public health benefits to mitigate the storage of excess sulfur in powder, or brick form.

Development of polymeric materials for infrared (IR) optical applications has not been achieved due to challenges in designing systems with sufficiently high refractive index (n) and transparency in the IR spectral regime. High refractive index polymers (HRIPs) are largely found in optical oriented devices, such as lenses. These HRIPs offer several significant advancements to older and current technologies in this field, such as lower densities, greater strengths, and overall increased performance. A higher "n" value indicates greater resistance to damage and breakage. Also, high-index lenses become lighter with an increasing n-value. For example, HRIPs allow for the production of thin lenses even for high prescriptions generally ranging from n=1.5 to n=1.8. Further, an increasing n-value would allow for lighter, more efficient frames (scopes) for these lenses. To date, organic plastics exhibit poor performance in the optical window of 1 to 10 µm due to strong IR absorption from the plastic material.

IR optical technology has numerous potential applications in the civil, medical, and military areas, with chalcogenide glasses and inorganic semiconductors (e.g., Ge, Si) being widely used as materials for device components due to their high refractive index (n~2.0-4.0) and low losses from 1-10 µm. Other examples of glass materials currently in use are InSb, InGaAs, HgCdTe, ArSe, and ArS. While such materials are well suited for these applications, they are more expensive, toxic, and difficult to process as compared to organic or organic/inorganic hybrid polymeric materials.

Although sulfur feedstocks are plentiful, sulfur is a difficult material to process. In its original form, elemental sulfur consists of a cyclic molecule having the chemical formulation $S_8$. Elemental sulfur is a brittle, intractable, crystalline solid having poor solid state mechanical properties, poor solution processing characteristics, and there are only a limited number of synthetic methods available to utilize and modify elemental sulfur. The inventors have previously developed a facile, one-step polymerization termed "inverse vulcanization" to prepare sulfur copolymers with a very high content of S—S bonds in the copolymer backbone ranging from 50-90 wt % sulfur that exhibited both high refractive index (n=1.9 to 1.7 from 600-1500 nm) and high IR transparency, in which further details can be found in co-owned U.S. Pat. No. 9,567,439 and U.S. Pat. No. 9,306,218, the specifications of which are incorporated herein in their entirety by reference.

Sulfur has a high refractive index, with n≥1.7 through the visible and IR spectra, which is significantly higher than all organic plastic materials. Moreover, the S—S bonds are largely IR inactive in this same optical window. Hence, the use of elemental sulfur as the chemical feedstock for these materials is desirable due to both the low cost of $S_8$ and favorable optical properties. However, since sulfur is difficult to process into films and molded objects, and previous synthetic methods have limited abilities to incorporate sulfur and create polymers with a high content of S—S bonds, there remains a need to improve the optical properties of said polymers to enable the development of materials for mid-IR applications.

3D printing, also known as additive layer manufacturing (ALM), typically comprises depositing, curing, fusing, or otherwise forming a material into sequential cross-sectional layers of the 3D object. Unlike milling that removes material to produce an object, ALM builds a solid object from a series of layers of material with each layer printed and formed on top of the previous layer. Examples of 3D printing techniques are generally disclosed in U.S. Pat. No. 4,749,347, U.S. Pat. No. 5,121,329, and U.S. Pat. No. 9,463,597, among others, which are incorporated by reference herein in their entirety.

Briefly, in the 3D printing process, a 3D printing device may comprise a dispenser, such as a dispenser head, that is capable of being moved in the x-, y-, and z-axes relative to a print pad. The print material is generally deposited out of the dispenser in layers in the x- and y-axes to form cross-sectional layers that are stacked along the z-axis to form the 3D object. In some embodiments, the print material may be in the form of a filament, liquid, gel, or powder form. The 3D printing device may be computer driven in a process utilizing computer aided design (CAD) or other computer software to generate drive signals for controlled movement of the dispenser and other components. Depending on the process that is used, many different types of materials can be used to form the patterned layers of the final product including, photopolymers, thermopolymers, plastics and metal powders. Current inorganic transmitting materials for IR imaging is extremely difficult to 3D print since it requires high temperatures to process said materials. Hence, there exists a need for materials that may be used for IR imaging and that are easily processable via 3D printing.

Currently, chalcogenide glasses are the primary material of choice for IR optics in the 3-5 micron range since all organic polymers strongly absorb in the IR optical regime. The present invention features chalcogenide-based copolymers that exhibit superior processing advantages over chalcogenide glasses since the chalcogenide-based copolymers can be solution or melt processed at relatively lower temperatures, which would make said copolymers compatible for 3D printing.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide polymeric materials that have a high refractive index of $n \geq 1.75$ in the visible and mid-IR regimes, high transparency in the mid-IR regime, and that can be amenable to 3D printing processes into lenses, films, or optical fibers. The present invention features a novel composition of incorporating selenium units into polymeric materials by copolymerizing sulfur with selenium with other comonomers to afford chalcogenide hybrid copolymers with refractive indices above $n \geq 1.75$, which is the key benchmark to warrant use of these polymeric transmitting materials in IR thermal imaging as lenses, windows and other devices.

Chalcogenide-based copolymers can utilize selenium to provide for the optical properties. Incorporation of selenium in the chalcogenic sulfur copolymer can greatly increase the refractive index of said copolymers. Using the inverse vulcanization method, the chalcogenic sulfur copolymers are shown to be a viable comonomer to prepare chemically stable polymer plastic materials with tunable optical and thermochemical properties by controlling the feed ratios of the chemical monomers added. The resulting chalcogenide-based sulfur copolymer may be fabricated into useful optical devices, such as films, waveguides, and molded (nano-, micro-) objects and lenses, via 3D printing.

One of the unique inventive technical features of the present invention is the use of elemental selenium or cyclic selenium sulfide as a precursor source for selenium units, and/or sulfur, that can be incorporated into high refractive index materials. Without wishing to limit the invention to any theory or mechanism, it is believed that this technical feature of the present invention advantageously provides for optical chalcogenic sulfur copolymers having ultra-high refractive indices ($n \geq 1.75$ in the visible and IR spectra) as compared to other polymers, and are readily melt processable for use in 3D printing techniques. This advantage allows for fabrication of otherwise inaccessible optical devices since current materials do not possess the optical and thermochemical properties of the present invention. None of the presently known prior references or works possess the unique inventive technical feature of the present invention. In fact, current HRIP materials that are commercially available have n-values typically ranging from $n=1.6$ to 1.75 in the visible spectrum.

Furthermore, the chalcogenic sulfur copolymer of the present invention may have the ability to self-heal upon reprocessing. Without wishing to limit the present invention to any particular theory or mechanism, it is believed that the self-healing property of these copolymers are due to their reversible S—S bonds, which allows for broken S—S bonds to be reconnected by methods such as heat processing. Any optical substrate constructed from these chalcogenic sulfur copolymers may be reprocessable and repairable.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

As used herein, sulfur can be provided as elemental sulfur, for example, in powdered form. Under ambient conditions, elemental sulfur primarily exists in an eight-membered ring form ($S_8$) which melts at temperatures in the range of 120°

C.-130° C. and undergoes an equilibrium ring-opening polymerization (ROP) of the $S_8$ monomer into a linear polysulfane with diradical chain ends. As the person of skill in the art will appreciate, while $S_8$ is generally the most stable, most accessible and cheapest feedstock, many other allotropes of sulfur can be used (such as other cyclic allotropes, derivable by melt-thermal processing of $S_8$). Any sulfur species that yield diradical or anionic polymerizing species when heated as described herein can be used in practicing the present invention.

As used herein, a "styrenic comonomer" is a monomer that has a vinyl functional group. The styrenic comonomer may comprise a styrene and at least one reactive functional group. As known to one of ordinary skill in the art, a styrene is a derivative of benzene ring that has a vinylic moiety. The sulfur diradicals can link to the vinylic moieties of the styrenic commoners to form the sulfur-styrenic polymer. In certain embodiments, the reactive functional group may be a halogen, an alkyl halide, an alkyl, an alkoxy, an amine, or a nitro functional group. Non-limiting examples of styrenic comonomers include bromostyrene, chlorostyrene, fluorostyrene, (trifluoromethyl)styrene, vinylaniline, acetoxystyrene, methoxystyrene, ethoxystyrene, methylstyrene, nitrostyrene, vinylbenzoic acid, vinylanisole, and vinylbenzyl chloride.

As used herein, the term "amine monomer" is a monomer that has an amine functional group. In one embodiment, aromatic amines and multi-functional amines may be used. Amine monomers include, but are not limited to, aromatic amines, m-phenylenediamine, and p-phenylenediamine. The various types of phenylenediamines are inexpensive reagents due to their wide-spread use in the preparation of many conventional polymers, e.g., polyureas, polyamides As used herein, the term "thiol monomer" is a monomer that has a thiol functional group. Thiol monomers include, but are not limited to, 4,4'-thiobisbenzenethiol and the like. The term "sulfide monomers" are monomers that have sulfide functional groups.

As used herein, an alkynylly unsaturated monomer is a monomer that has an alkynylly unsaturated functional group (i.e. triple bond). The term "alkynylly unsaturated monomer" does not include compounds in which the alkynyl unsaturation is part of a long chain alkyl moiety (e.g., unsaturated fatty acids, or carboxylic salts, or esters such as oleates, and unsaturated plant oils). In one embodiment, aromatic alkynes, both internal and terminal alkynes, multi-functional alkynes may be used. Examples of alkynylly unsaturated monomers include, but are not limited to, ethynylbenzene, 1-phenylpropyne, 1,2-diphenylethyne, 1,4-diethynylbenzene, 1,4-bis(phenylethynyl) benzene, and 1,4-diphenylbuta-1,3-diyne.

As used herein, the term "nitrone monomer" is a monomer that has a nitrone groups. In one embodiment, nitrones, dinitrones, and multi-nitrones may be used.

Examples include, but are not limited to, N-benzylidene-2-methylpropan-2-amine oxide.

As used herein, the term "aldehyde monomer" is a monomer that has an aldehyde functional group. In one embodiment, aldehydes, dialdehydes, and multi-aldehydes may be used.

As used herein, the term "ketone monomer" is a monomer that has a ketone functional group. In one embodiment, ketones, di-ketones, and multi-ketones may be used.

As used herein, the term "epoxide monomer" is a monomer that has epoxide functional groups. Non-limiting examples of such monomers include, generally, mono- or polyoxiranylbenzenes, mono- or polyglycidylbenzenes, mono- or polyglycidyloxybenzenes, mono- or polyoxiranyl (hetero)aromatic compounds, mono- or polyglycidyl(hetero) aromatic compounds, mono- or polyglycidyloxy(hetero)aromatic compounds, diglycidyl bisphenol A ethers, mono- or polyglycidyl(cyclo)alkyl ethers, mono- or polyepoxy(cyclo) alkane compounds and oxirane-terminated oligomers. In one preferred embodiment, the epoxide monomers may be benzyl glycidyl ether and tris(4-hydroxyphenyl)methane triglycidyl ether. In certain embodiments, the epoxide monomers may include a (hetero)aromatic moiety such as, for example, a phenyl, a pyridine, a triazine, a pyrene, a naphthalene, or a polycyclic (hetero)aromatic ring system, bearing one or more epoxide groups. For example, in certain embodiments, the one or more epoxide monomers are selected from epoxy(hetero)aromatic compounds, such as styrene oxide and stilbene oxide and (hetero)aromatic glycidyl compounds, such as glycidyl phenyl ethers (e.g., resorcinol diglycidyl ether, glycidyl 2-methylphenyl ether), glycidylbenzenes (e.g., (2,3-epoxypropyl)benzene) and glycidyl heteroaromatic compounds (e.g., N-(2,3-epoxypropyl)phthalimide). In certain desirable embodiments, an epoxide monomer will have a boiling point greater than 180° C., greater than 200° C., or even greater than 230° C. at the pressure at which polymerization is performed (e.g., at standard pressure, or at other pressures).

As used herein, the term "thiirane monomer" is a monomer that has a thirane functional group. Non-limiting examples of thiirane monomers include, generally, mono- or polythiiranylbenzenes, mono- or polythiiranylmethylbenzenes, mono- or polythiiranyl(hetero)aromatic compounds, mono- or polythiiranylmethyl(hetero)-aromatic compounds, dithiiranylmethyl bisphenol A ethers, mono- or polydithiiranyl (cyclo)alkyl ethers, mono- or polyepisulfide(cyclo) alkane compounds, and thiirane-terminated oligomers. In some embodiments, thiirane monomers may include a (hetero)aromatic moiety such as, for example, a phenyl, a pyridine, a triazine, a pyrene, a naphthalene, or a poly cyclic (hetero)aromatic ring system, bearing one or more thiirane groups. In certain desirable embodiments, a thiirane monomer can have a boiling point greater than 180° C., greater than 200° C., or even greater than 230° C. at the pressure at which polymerization is performed (e.g., at standard pressure).

As used herein, an ethylenically unsaturated monomer is a monomer that contains an ethylenically unsaturated functional group (i.e. double bond). The term "ethylenically unsaturated monomer" does not include cyclopentadienyl species such as cyclopentadiene and dicyclopentadiene. The term "ethylenically unsaturated monomer" does not include compounds in which the ethylenic unsaturation is part of a long chain alkyl moiety (e.g. unsaturated fatty acids such as oleates, and unsaturated plant oils).

Non-limiting examples of ethylenically unsaturated monomers include vinyl monomers, acryl monomers, (meth)acryl monomers, unsaturated hydrocarbon monomers, and ethylenically-terminated oligomers. Examples of such monomers include, generally, mono- or polyvinylbenzenes, mono- or polyisopropenylbenzenes, mono- or polyvinyl(hetero)aromatic compounds, mono- or polyisopropenyl(hetero)-aromatic compounds, acrylates, methacrylates, alkylene di(meth)acrylates, bisphenol A di(meth)acrylates, benzyl (meth)acrylates, phenyl(meth)acrylates, heteroaryl (meth)acrylates, terpenes (e.g., squalene) and carotene. In other embodiments, the ethylenically unsaturated monomers may include a (hetero)aromatic moiety such as, for example, phenyl, pyridine, triazine, pyrene, naphthalene, or a polycyclic (hetero)aromatic ring system, bearing one or more vinylic, acrylic or methacrylic substituents. Examples of such monomers include benzyl (meth)acrylates, phenyl (meth)acrylates, divinylbenzenes (e.g., 1,3-divinylbenzene, 1,4-divinylbenzene), isopropenylbenzene, styrenics (e.g., styrene, 4-methylstyrene, 4-chlorostyrene, 2,6-dichlorostyrene, 4-vinylbenzyl chloride). diisopropenylbenzenes (e.g., 1,3-diisopropenylbenzene), vinylpyridines (e.g., 2-vinylpyridine, 4-vinylpyridine), 2,4,6-tris((4-vinylbenzyl)thio)-1,3,5-triazine and divinylpyridines (e.g., 2,5-divinylpyridine). In certain embodiments, the ethylenically unsaturated monomers (e.g., including an aromatic moiety) bear an amino (i.e., primary or secondary) group, a phosphine group or a thiol group. One example of such a monomer is vinyldiphenylphosphine. In certain desirable embodiments, an ethylenically unsaturated monomer will have a boiling point greater than 180° C. greater than 200° C., or even greater than 230° C. at the pressure at which polymerization is performed (e.g., at standard pressure).

As used herein, the term "self-healing" is defined as to enable a material to repair damage with minimum intervention. In some embodiments, mechanisms and techniques to enable self-healing may include covalent bonding, supramolecular chemistry, H-bonding, ionic interactions, π-π stacking, chemo-mechanical repairs focusing on encapsulation, remote self-healing, or shape memory assisted polymers. In one preferred embodiment, self-healing utilizes thermal reformation. As used herein, thermal reformation involves the use of heat to reform the bonds or cross-links of a polymeric material.

As used herein, the term "functional" in correlation with a polymer refers to functional polymers that have specified physical, chemical, biological, pharmacological, or other properties or uses that are determined by the presence of specific chemical functional groups, which are usually dissimilar to those of the backbone chain of the polymer.

As used herein, the term "chalcogenide" refers to a compound containing one or more chalcogen elements. One of ordinary skill in the art will understand that the classical chalcogen elements are sulfur, selenium and tellurium. In accordance with the present invention, the use of chalcogenide refers to compounds and/or polymers containing selenium.

As known to one of ordinary skill in the art, the term "isomer" refers to compounds having the same formula but differ in arrangement. For instance, isomers of cyclic selenium sulfides, such as $Se_2S_6$ and $Se_3S_5$, can have different placements of the Se units in the ring (e.g., S—Se—Se—S or S—Se—S). Isomers of $Se_2S_6$ include 1,2-isomers, 1,3-isomers, 1,4-isomers, and 1,5-isomers, wherein the numbers refer to the position of the Se units in the eight-membered ring.

As known to one of ordinary skill in the art, the term "visible" refers to a portion of the electromagnetic spectrum that falls in the range of 390 to 700 nm. As used herein, the term "infrared" (IR) refers to a portion of the electromagnetic spectrum that falls in the range of 700 nm to 1 mm. Subsets of the IR spectrum include near-IR (700 nm to 3 μm), mid-IR (3-8 μm), long-wavelength IR (8-15 μm) and far-IR (15 μm to 1 mm).

As used herein, the terms "those defined above" and "those defined herein" when referring to a variable incorporates by reference the broad definition of the variable as well as any narrow and/or preferred, more preferred and most preferred definitions, if any.

Referring now to FIGS. 1-5, the chalcogenic sulfur copolymers that are described herein are the first class of polymeric materials that exhibit high transparency in the short-wave and mid-IR regimes due to the presence of largely IR inactive S—S bonds. Furthermore, since these chalcogenic sulfur copolymers are readily melt, or solution processed, fabrication of free standing films, windows, or lenses can be easily conducted via 3D printing. Access to these kinds of high quality and inexpensive lenses are anticipated to open new opportunities in low cost IR optical devices and technologies including IR thermal imaging rifle scopes and home monitoring.

According to one embodiment, the present invention features a method of producing a substrate using 3D printing. The method may comprise providing a print material comprising a sulfur copolymer, introducing said print material into a 3D printer, and dispensing said print material by successively applying layers of said print material to form the substrate. In preferred embodiments, the substrate produced from the print material can have a refractive index of about 1.75-2.6 at a wavelength in a range of about 500 nm to about 8 μm.

In some embodiments, the sulfur copolymer may comprise one or more chalcogenic monomers at a level of at least 50 wt % of the sulfur copolymer, and one or more comonomers at a level in the range of about 5-50 wt % of the sulfur copolymer. In preferred embodiments, the chalcogenic monomers may comprise at least sulfur units. In other preferred embodiments, the chalcogenic monomers may comprise sulfur and selenium units. For instance, the chalcogenic monomers may comprise elemental sulfur, liquid polysulfide, cyclic selenium sulfide and isomers thereof, oligomers containing sulfur, or oligomers containing sulfur and selenium units. In some embodiments, the oligomer containing sulfur and selenium units may be derived from elemental sulfur and elemental selenium (e.g., $Se_8$, polymeric selenium). In one embodiment, the sulfur copolymer may comprise at least about 30 wt % of sulfur. In another embodiment, the sulfur copolymer may comprise at least about 30 wt % of elemental selenium.

In some embodiments, the chalcogenic monomers may be polymerized with the one or more comonomers via free radical polymerization, controlled radical polymerization, ring-opening polymerization, ring-opening metathesis polymerization, step-growth polymerization, or chain-growth polymerization. Polymerizing the chalcogenic monomers with the comonomers enables at least one functional sulfur moiety of the chalcogenic monomers to bond with at least one functional moiety of the one or more monomers.

According to a non-limiting embodiment, the sulfur copolymer may comprise one or more cyclic selenium sulfide monomers having the formula $Se_nS_{(8-n)}$, and one or more comonomers at a level in the range of about 5-50 wt % of the sulfur copolymer. In another embodiment, the cyclic selenium sulfide monomers comprises at most about 70 wt % of selenium, and can include any isomer of the formula.

In some embodiments, n in an integer that can range from 1 to 7. For example, when n=2, the cyclic selenium sulfide monomers have the formula $Se_2S_6$. As another example, when n=3, the cyclic selenium sulfide monomers have the formula $Se_3S_5$. Preferably, the one or more cyclic selenium sulfide monomers can comprise all possible isomers of a specific formula. In alternative embodiments, the selenium sulfide monomers can be of the formula $Se_nS_m$, wherein n ranges from 1 to 7 and m ranges from 1 to 7, wherein the selenium sulfide monomers are not necessarily cyclic. In one embodiment, assuming that n=7, i.e. $Se_7S$, then the cyclic selenium sulfide monomers may comprise at most about 70 wt % of selenium.

In some embodiments, the cyclic selenium sulfide monomers are polymerized with the one or more comonomers via free radical polymerization, controlled radical polymerization, ring-opening polymerization, ring-opening metathesis polymerization, step-growth polymerization, or chain-growth polymerization. In preferred embodiments, polymerizing the comonomers with the selenium sulfide enables at least one functional sulfur moiety of the selenium sulfide to bond with at least one functional moiety of the one or more monomers.

In one embodiment, the sulfur copolymer may comprise one or more cyclic selenium sulfide monomers at a range of about 5 to 10 wt %, or about 10 to 20 wt %, or about 20 to 30 wt %, or about 30 to 40 wt %, or about 40 to 50 wt %, or about 50 to 60 wt %, or about 60 to 70 wt % of the sulfur copolymer. In another embodiment, the cyclic selenium sulfide monomers may comprise selenium units of at most about 20 wt %, or at most about 30 wt %, or at most about 40 wt % or at most about 50 wt %, or at most about 60 wt %, or at most about 70 wt % of the cyclic selenium sulfur monomers. In a further embodiment, the cyclic selenium sulfide monomers comprises at most about 70 wt % of selenium. In some embodiments, the one or more comonomers are at a range of about 5 to 10 wt %, or about 10 to 20 wt %, or about 20 to 30 wt %, or about 30 to 40 wt %, or about 40 to 50 wt % of the sulfur copolymer.

In other embodiments, the sulfur copolymer may further comprise about 5-50 wt % of elemental sulfur ($S_8$). In other embodiments, the elemental sulfur can be at a range of about 5 to 10 wt %, or about 10 to 20 wt %, or about 20 to 30 wt %, or about 30 to 40 wt %, or about 40 to 50 wt % of the sulfur copolymer.

In still other embodiments, the sulfur copolymer may further comprise about 5-50 wt % of elemental selenium (e.g., $Se_8$, polymeric selenium). In further embodiments, the elemental selenium can be at a range of about 5 to 10 wt %, or about 10 to 20 wt %, or about 20 to 30 wt %, or about 30 to 40 wt %, or about 40 to 50 wt % of the sulfur copolymer. For instance, the sulfur copolymer may comprise 30 wt % S, 35 wt % cyclic selenium-sulfide, and 35 wt % 1,3 diisopropenyl benzene.

According to another non-limiting embodiment, the sulfur copolymer may comprise one or more sulfur monomers derived from elemental sulfur at a level of at least 30 wt % of the sulfur copolymer, elemental selenium (e.g., $Se_8$, polymeric selenium)) at a level of at least 30 wt % of the sulfur copolymer, and one or more comonomers at a level in the range of about 5-50 wt % of the sulfur copolymer. In one embodiment, the sulfur copolymer may comprise at least about 50 wt % sulfur monomers. In another embodiment, the sulfur copolymer may comprise at least about 50 wt % of elemental selenium. In an exemplary embodiment, the sulfur copolymer may comprise about 30-50 wt % of sulfur monomers, about 30-50 wt % of elemental selenium, and about 15-25 wt % of the comonomers, such as diisopropenylbenzene.

According to another embodiment, the sulfur copolymer may comprise one or more sulfur monomers derived from elemental sulfur at a level of at least 30% wt of the sulfur copolymer, and one or more comonomers at a level in the range of about 5-50 wt % of the sulfur copolymer. In some embodiments, the sulfur copolymer comprises at least about 50 wt % sulfur monomers. In other embodiments, the one or more comonomers are at a range of about 5 to 10 wt %, or about 10 to 20 wt %, or about 20 to 30 wt %, or about 30 to 40 wt %, or about 40 to 50 wt % of the sulfur copolymer. In still other embodiments, the sulfur copolymer may further comprise at least about 30 wt %, or at least about 40 wt %, or at least about 50 wt % of elemental selenium (e.g., $Se_8$, polymeric selenium).

In some embodiments, the sulfur monomers are polymerized with the one or more comonomers via free radical polymerization, controlled radical polymerization, ring-opening polymerization, ring-opening metathesis polymerization, step-growth polymerization, or chain-growth polymerization. In preferred embodiments, polymerizing the comonomers with the sulfur monomers enables at least one functional sulfur moiety of the sulfur monomers to bond with at least one functional moiety of the one or more monomers.

Consistent with previous embodiments of the sulfur copolymer, the one or more comonomers may be amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers. maleimide monomers, norbornene monomers, monomers having at least one vinyl ether moiety, or monomers having at least one isopropenyl moiety.

In yet other embodiments, the sulfur copolymer may further comprise one or more termonomers. In some embodiments, the termonomers may be a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, or a styrenic monomer. The termonomers may be present in an amount ranging from about 5 to 50 wt % of the sulfur copolymer.

In still other embodiments, the sulfur copolymer may further comprise one or more polyfunctional monomers, such as for example, a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, or a polyethylenically unsaturated monomer. The polyfunctional monomers may be present in an amount ranging from about 5 to 50 wt % of the sulfur copolymer.

In some embodiments, the print material may be dispensed through a dispenser of the 3D printer. The dispenser may comprise a heated nozzle and the print material is supplied to the heated nozzle in a solid state and dispensed from the heated nozzle in a generally liquid state. In other embodiments, the step of dispensing said print material may comprise extruding said print material to form a filament, melting the filament in a dispenser of the 3D printer, and depositing the molten material in successive layers to produce the substrate.

In other embodiments, the print material is a form of a liquid, gel, or powder. In some embodiments, the method of producing a substrate may further comprise dispensing a binding material, such as water, an adhesive, or a resin, to each layer of print material. In other embodiments, the method of producing a substrate may further comprise activating the print material via thermal, chemical, thermochemical, or photo/light activation, thereby hardening the print material to form the substrate. In some other embodiments, the print material may be activated by IR photo-heating or photo-patterning to harden the print material. In one embodiment, an IR laser can be used to shape the 3D substrate of print material.

According to some embodiments, the substrate produced from the print material is substantially transparent in an infrared or visible spectrum. For instance, the substrate may be substantially transparent in a spectrum having a wavelength range of about 1000-1500 nm, or 1500-3000 nm. or about 3000-5000 nm, or about 5-10 microns. Preferably, the sulfur copolymer can be formed into a substantially transparent substrate, such as a film, a lens, or a free-standing object. In another embodiment, the substrate may be an optical device component, such as lens, a window, a microlens array, a waveguide, a Bragg reflector, or an optical fiber, configured for use as a transmitting material in an infrared imaging device.

According to another embodiment, the present invention features a print material comprising a liquid polysulfide, a liquid chalcogenide polymer, or oligomer containing sulfur or selenium units, which is synthesized to incorporate photocurable moieties such as vinyl, epoxide, azide, cinnamate, coumarin, benzophenone and other unsaturated moieties. These functional photocurable liquid polymers can be 3D printed via stereolithography. For example, the liquid polymers are photopolymerized upon exposure to UV or visible irradiation through a nozzle/syringe feed, or through a transparent monomer reservoir with an external light source, to prepare high refractive index polymers (n≥1.75).

As known to one of ordinary skill in the art, stereolithography is a 3D printing process where an excess of liquid polymer is photocured or hardened to form a solid substrate. For example, a UV laser may be used to "print", i.e. cure, each cross-sectional layer of the substrate. The UV laser selectively traces each cross-section, which bonds to the hardened section beneath it. This process is repeated until the entire substrate has been formed. In some embodiments, the completed substrate may be further cured in a UV oven. In other embodiments, the liquid polymer may be photocured, hardened, or activated by IR photo-heating or photo-patterning to form the 3D substrate. An IR laser can be used to activate and shape/form the 3D substrate.

Accordingly to some embodiments, the present invention features a method of producing a substrate using 3D printing, comprising providing a liquid print material comprising a sulfur copolymer having photocurable moieties, adding said liquid print material into a reservoir, and selectively photopolymerizing said print material in the reservoir to produce the substrate. Preferably, the photocurable moieties enable photopolymerization of said print material. Even more preferably, the substrate produced from the print material has a refractive index of about 1.75-2.6 at a wavelength in a range of about 500 nm to about 8 µm.

In some embodiments, the sulfur copolymer may be any of the sulfur copolymers described herein. For example, the sulfur copolymer may comprise a liquid polysulfide, a liquid chalcogenide polymer, cyclic selenium sulfide, an oligomer containing sulfur, or an oligomer containing sulfur and selenium units, copolymerized with the one or more monomers.

In one embodiment, the photocurable moieties of the sulfur copolymer may be vinyl, epoxide, azide, cinnamate, coumarin, benzophenone, or other unsaturated moieties. In some embodiments, the print material is photopolymerized upon exposure to UV or visible irradiation. In other embodiments, the print material is selectively photopolymerized in layers.

According to another embodiment, the present invention features a print material for 3D printing. The print material may comprise a sulfur copolymer. In some embodiments, the sulfur copolymer may comprise one or more chalcogenic monomers at a level of at least 50 wt % of the sulfur copolymer, and one or more comonomers at a level in the range of about 5-50 wt % of the sulfur copolymer. In preferred embodiments, the chalcogenic monomers may comprise at least sulfur units. In other preferred embodiments, the chalcogenic monomers may comprise sulfur and selenium units. For instance, the chalcogenic monomers may comprise elemental sulfur, liquid polysulfide, cyclic selenium sulfide and isomers thereof, oligomers containing sulfur, or oligomers containing sulfur and selenium units. In some embodiments, the oligomer containing sulfur and selenium units may be derived from elemental sulfur and elemental selenium (e.g., $Se_8$, polymeric selenium). In one embodiment, the sulfur copolymer may comprise at least about 30 wt % of sulfur. In another embodiment, the sulfur copolymer may comprise at least about 30 wt % of elemental selenium.

In another embodiment, the print material may comprise a sulfur copolymer comprising one or more cyclic selenium sulfide monomers having the formula $Se_nS_{(8-n)}$, and one or more comonomers In some embodiments, the cyclic selenium sulfide monomers comprises at most about 70 wt % of selenium. In some embodiments, n in an integer ranging from 1 to 7. In other embodiments, the one or more comonomers are at a level in the range of about 5-50 wt % of the sulfur copolymer. In other embodiments, at least one functional sulfur moiety of the selenium-sulfide is bonded to at least one functional moiety of the one or more monomers. In one embodiment, the sulfur copolymer may further comprise one or more sulfur monomers derived from elemental sulfur ($S_8$, at a level of about 5-50 wt % of the sulfur copolymer. In another embodiment, the sulfur copolymer may further comprise elemental selenium (e.g., $Se_8$, polymeric selenium), at a level of about 5-50 wt % of the sulfur copolymer.

According to some embodiments, the print material may comprise a sulfur copolymer comprising one or more sulfur monomers derived from elemental sulfur at a level of at least 30 wt % of the sulfur copolymer, elemental selenium (e.g., $Se_8$, polymeric selenium) at a level of at least 30 wt % of the sulfur copolymer, and one or more comonomers at a level in the range of about 5-50 wt % of the sulfur copolymer. In one embodiment, the sulfur copolymer may comprise at least about 50 wt % sulfur monomers. In another embodiment, the sulfur copolymer may comprise at least about 50 wt % of elemental selenium. In an exemplary embodiment, the sulfur copolymer may comprise about 30-50 wt % of sulfur monomers, about 30-50 wt % of elemental selenium, and about 15-25 wt % of the comonomers, such as diisopropenylbenzene.

According to other embodiments, the print material may comprise a sulfur copolymer comprising one or more sulfur monomers derived from elemental sulfur at a level of at least 30% wt of the sulfur copolymer, and one or more comonomers at a level in the range of about 5-50 wt % of the sulfur copolymer. In some embodiments, the sulfur monomers may be at least about 50 wt %. In other embodiments, the sulfur copolymer may further comprise at least about 30 wt %, or at least about 40 wt %, or at least about 50 wt % of elemental selenium (e.g., $Se_8$, polymeric selenium).

According to yet other embodiments, the print material may comprise a sulfur copolymer having photocurable moieties that enable photopolymerization of said print material. The sulfur copolymer may be a liquid polysulfide, a liquid chalcogenide polymer, cyclic selenium sulfide, an oligomer containing sulfur, or an oligomer containing sulfur and selenium units, copolymerized with the one or more monomers. The photocurable moieties of the sulfur copolymer may be vinyl, epoxide, azide, cinnamate, coumarin, benzophenone, or other unsaturated moieties.

Consistent with previous embodiments of the print material, the one or more comonomers may be amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, or monomers having at least one isopropenyl moiety.

In one embodiment, the sulfur copolymer may further comprise one or more termonomers at about 5 to 50 wt % of the sulfur copolymer. Examples of termonomers include, but are not limited to, a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, or a styrenic monomer.

In another embodiment, the sulfur copolymer may further comprise one or more polyfunctional monomers at about 5 to 50 wt % of the sulfur copolymer. Examples of polyfunctional monomers include, but are not limited to, a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, and a polyethylenically unsaturated monomer.

In preferred embodiments, the print material is formed into a substantially transparent substrate via 3D printing. The transparent substrate can be a film, a lens, or a freestanding object. Alternatively, the substrate may an optical device component configured for use as a transmitting material in an infrared imaging device, such as for example, a lens, a window, a microlens array, a waveguide, a Bragg reflector, or an optical fiber. In preferred embodiments, the substrate has a refractive index of about 1.75-2.6 at a wavelength in a range of about 500 nm to about 8 µm. In yet other embodiments, the print material is self-healing upon thermal reprocessing.

In some embodiments, the substrate produced from the print material is substantially transparent in an infrared or visible spectrum. In other embodiments, the substrate produced from the print material is substantially transparent in a spectrum having a wavelength range of about 1000-1500 nm. In yet other embodiments, the substrate produced from the print material is substantially transparent in a spectrum having a wavelength range of about 3000-5000 nm. In further embodiments, the substrate produced from the print material is substantially transparent in a spectrum having a wavelength range of about 5-10 microns.

According to another embodiment, the invention features a method of making an optical substrate. The method may comprise 3D printing said optical substrate using any of the print material described herein. In preferred embodiments, the optical substrate is substantially transparent and has a refractive index of about 1.75-2.6 at a wavelength in a range of about 500 nm to about 8 µm.

According to another embodiment, the present invention features a method of preparing a print material for use in a 3D printer. The method may comprise preparing a sulfur copolymer, and forming the sulfur copolymer to the print material in a form suitable for use in the 3D printer.

In some embodiments, the step of preparing the sulfur copolymer may comprise providing at least 50 wt % of chalcogenic monomers, heating the cyclic chalcogenic monomers to form a liquid chalcogenic solution, adding about 5-50 wt % of one or more comonomers to the liquid chalcogenic solution, and polymerizing the comonomers with the liquid chalcogenic solution to form the sulfur copolymer. In other embodiments, the step of preparing the sulfur copolymer further comprises heating the sulfur copolymer until the sulfur copolymer is substantially vitrified.

In some embodiments, the chalcogenic monomers may comprise at least sulfur units. In other embodiments, the chalcogenic monomers may comprise sulfur and selenium units. For instance, the chalcogenic monomers may comprise elemental sulfur, liquid polysulfide, cyclic selenium sulfide and isomers thereof, oligomers containing sulfur, or oligomers containing sulfur and selenium units. In some embodiments, the oligomer containing sulfur and selenium units may be derived from elemental sulfur and elemental selenium (e.g., $Se_8$, polymeric selenium). In one embodiment, the sulfur copolymer may comprise at least about 30 wt % of sulfur. In another embodiment, the sulfur copolymer may comprise at least about 30 wt % of elemental selenium.

In some other embodiments, the step of preparing the sulfur copolymer may comprise providing cyclic selenium sulfide having the formula $Se_nS_{(8-n)}$, wherein the cyclic selenium sulfide monomers comprises at most about 70 wt % of selenium, heating the cyclic selenium sulfide to form a liquid selenium sulfide, adding about 5-50 wt % of one or more comonomers to the liquid selenium sulfide, and polymerizing the comonomers with the liquid selenium sulfide to form the sulfur copolymer. In other embodiments, the step of preparing the sulfur copolymer further comprises heating the sulfur copolymer until the sulfur copolymer is substantially vitrified.

In some embodiments, n in an integer that can range from 1 to 7. For example, when n=2, the cyclic selenium sulfide can have the formula $Se_2S_6$. As another example, when n=3, the cyclic selenium sulfide can have the formula $Se_3S_5$. Preferably, the cyclic selenium sulfide can comprise all possible isomers of a specific formula. In alternative embodiments, the selenium sulfide can be of the formula $Se_nS_m$, wherein n ranges from 1 to 7 and m ranges from 1 to 7, wherein the selenium sulfide are not necessarily cyclic.

In other embodiments, the step of producing the sulfur copolymer may further comprise adding about 5-50 wt % of elemental sulfur to the cyclic selenium sulfide prior to adding the comonomers. In yet other embodiments, the step of producing the sulfur copolymer may further comprise adding about 5-50 wt % of elemental selenium to the cyclic selenium sulfide prior to adding the comonomers.

According to some embodiments, the step of preparing the sulfur copolymer may comprise providing at least 30 wt % of elemental sulfur, heating the elemental sulfur to form molten sulfur, adding at least 30 wt % of elemental selenium (e.g., $Se_8$, polymeric selenium) to the molten sulfur to form a liquid selenium sulfur mixture, adding about 5-50 wt % of one or more comonomers to the liquid selenium sulfur mixture, and polymerizing the comonomers with the liquid selenium sulfur mixture to form the sulfur copolymer. In one embodiment, the step of preparing the sulfur copolymer may further comprise heating the sulfur copolymer until the sulfur copolymer is substantially vitrified. In another embodiment, the step of preparing the sulfur copolymer comprises providing at least about 50 wt % of elemental sulfur. In yet another embodiment, the step of preparing the sulfur copolymer comprises adding at least about 50 wt % of elemental selenium. In a further embodiment, the sulfur copolymer may comprise about 30-50 wt % of elemental sulfur, about 30-50 wt % of elemental selenium, and about 15-25 wt % of the comonomers.

According to other embodiments, the step of preparing the sulfur copolymer may comprise providing at least about 30 wt % elemental sulfur, melting the elemental sulfur to form a molten sulfur, adding about 5-50 wt % of one or more comonomers to the molten sulfur, and polymerizing the comonomers with the molten sulfur to form the sulfur copolymer. In some embodiments, the step of preparing the sulfur copolymer may further comprise heating the sulfur copolymer until the sulfur copolymer is substantially vitrified. In other embodiments, the step of preparing the sulfur copolymer comprises providing at least about 50 wt % of elemental sulfur. In still other embodiments, the step of preparing the sulfur copolymer may further comprise adding at least about 30 wt %, or about 40 wt %, or about 50 wt % of elemental selenium prior to adding the comonomers.

Consistent with previous embodiments of preparing the sulfur copolymer, the one or more comonomers may be amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, or monomers having at least one isopropenyl moiety.

In some embodiments, the sulfur copolymer is prepared such that available photocurable moieties are incorporated into the sulfur copolymer. The photocurable moieties may be vinyl, epoxide, azide, cinnamate, coumarin, benzophenone, or other unsaturated moieties.

Examples of techniques of polymerizing include, but are not limited to, free radical polymerization, controlled radical polymerization, ring-opening polymerization, ring-opening metathesis polymerization, step-growth polymerization, and chain-growth polymerization.

In other embodiments, the step of preparing the sulfur copolymer may further comprise polymerizing the sulfur copolymer with one or more termonomers. The one or more termonomers can be a vinyl monomer, an isopropenyl monomer, an acryl monomer, a methacryl monomer, an unsaturated hydrocarbon monomer, an epoxide monomer, a thiirane monomer, an alkynyl monomer, a diene monomer, a butadiene monomer, an isoprene monomer, a norbornene monomer, an amine monomer, a thiol monomer, a sulfide monomer, an alkynylly unsaturated monomer, a nitrone monomer, an aldehyde monomer, a ketone monomer, an ethylenically unsaturated monomer, or a styrenic monomer. The termonomers may be present in an amount ranging from about 5 to 50 wt % of the sulfur copolymer.

In still other embodiments, the step of preparing the sulfur copolymer may further comprise polymerizing the sulfur copolymer with one or more polyfunctional monomers. The one or more polyfunctional monomers can be a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomer, a polynitrone monomer, a polyaldehyde monomer, a polyketone monomer, or a polyethylenically unsaturated monomer. The polyfunctional monomers may be present in an amount ranging from about 5 to 50 wt % of the sulfur copolymer.

In some embodiments, the step of forming the sulfur copolymer may comprise extruding the sulfur copolymer such that the print material is in the form of filaments. In other embodiments, the step of forming the sulfur copolymer comprises grinding the sulfur copolymer such that the print material is in the form of a powder. In further embodiments, the step of forming the sulfur copolymer comprises liquefying, i.e. dissolving in a solvent or melting, the sulfur copolymer such that the print material is in the form of a gel or liquid.

According to some embodiments, the print material can be formed into a substantially transparent substrate, such as a film, a lens, or a free-standing object, via 3D printing. The substrate may be substantially transparent in an infrared or visible spectrum. For instance, the substrate may substantially transparent in a spectrum having a wavelength range of about 1000-1500 nm, or 1500-3000 nm. or about 3000-5000 nm, or about 5-10 microns. In another embodiment, the print material can be fabricated into an optical device component via 3D printing for use as a transmitting material in an infrared imaging device. The optical device component can be a lens, a window, a microlens array, a waveguide, a Bragg reflector, or an optical fiber.

According to another embodiment, a thermoplastic form of the sulfur containing polymer as described herein may be is pre-processed into a fibrous form that is then 3D printed via fused filament modelling into free standing substrates. Examples of said free standing substrates include, but are not limited to, optic substrates, optical components and optical devices such as lenses, windows, fibers, waveguides, microlens arrays, and Bragg reflectors.

In some embodiments, the sulfur copolymer is a thermoset. In some embodiments, the sulfur copolymer is a thermoplastic. In some embodiments, the sulfur copolymer is self-healing. In some embodiments, when one or more S—S bonds of the sulfur copolymer are broken, the S—S bonds are reconnected by thermal reforming.

In some embodiments, the present invention may feature a method of repairing an optical substrate, said method comprising providing the optical substrate comprising a sulfur copolymer having one or more broken S—S bonds, and heat treating the optical substrate at a healing temperature for a period of time in order to reconnect the S—S bonds of the sulfur copolymer. In some embodiments, the healing temperature is between about 80° C. and 100° C. In other embodiments, the healing temperature is between about 100° C. and 150° C. In some embodiments, the healing temperature is at or near the melting point of the polymeric substrate. In some embodiments, the period of time is between about 4 and 15 hours. In other embodiments, the period of time is between about 8 and 12 hours.

EXAMPLES

For illustrative purposes, the following are non-limiting examples of preparing the sulfur copolymers of the present invention. Equivalents or substitutes are within the scope of the invention.

Example 1

Synthesis of poly(sulfur-random-selenium-random-(1,3-diisopropenyibenzene).

To an 11 ml scintillation vial, equipped with a magnetic stir bar, was loaded with about 1.4 g (70 wt %, 2.0 g scale) Selenium Sulfide ($Se_nS_m$; 1.4 g) and about 0.65 mL (30 wt %, 2.0 g scale, d(DIB)=0.925 g/mL) 1,3-diisopropenylbenzene (DIB). The contents of the vial were mixed via a vortex for about 3 minutes. The vial was then lowered into a 180° C. thermostated oil bath (set to 850 rpm) for about 80 minutes. The vial was then removed from the oil bath and allowed to cool to RT.

Example 2

Synthesis of S—$Se_nS_m$-DIB

To a scintillation vial, equipped with a magnetic stir bar, was loaded with about 40% wt elemental sulfur, 30% wt selenium sulfide, and 30% wt DIB. The contents of the vial were mixed via a vortex for about 3 minutes. The vial was then lowered into a 180 thermostated oil bath (set to 850 rpm) for about 80 minutes. The vial was then removed from the oil bath and allowed to cool to RT.

Example 3

Synthesis of S—$Se_nS_m$-DIB-Se

To a scintillation vial, equipped with a magnetic stir bar, was loaded with about 40% wt elemental sulfur, 30% wt selenium sulfide, 20% wt DIB, and 10% wt elemental selenium. The contents of the vial were mixed via a vortex for about 3 minutes. The vial was then lowered into a 180° C. thermostated oil bath (set to 850 rpm) for about 80 minutes. The vial was then removed from the oil bath and allowed to cool to RT.

Figure 1:
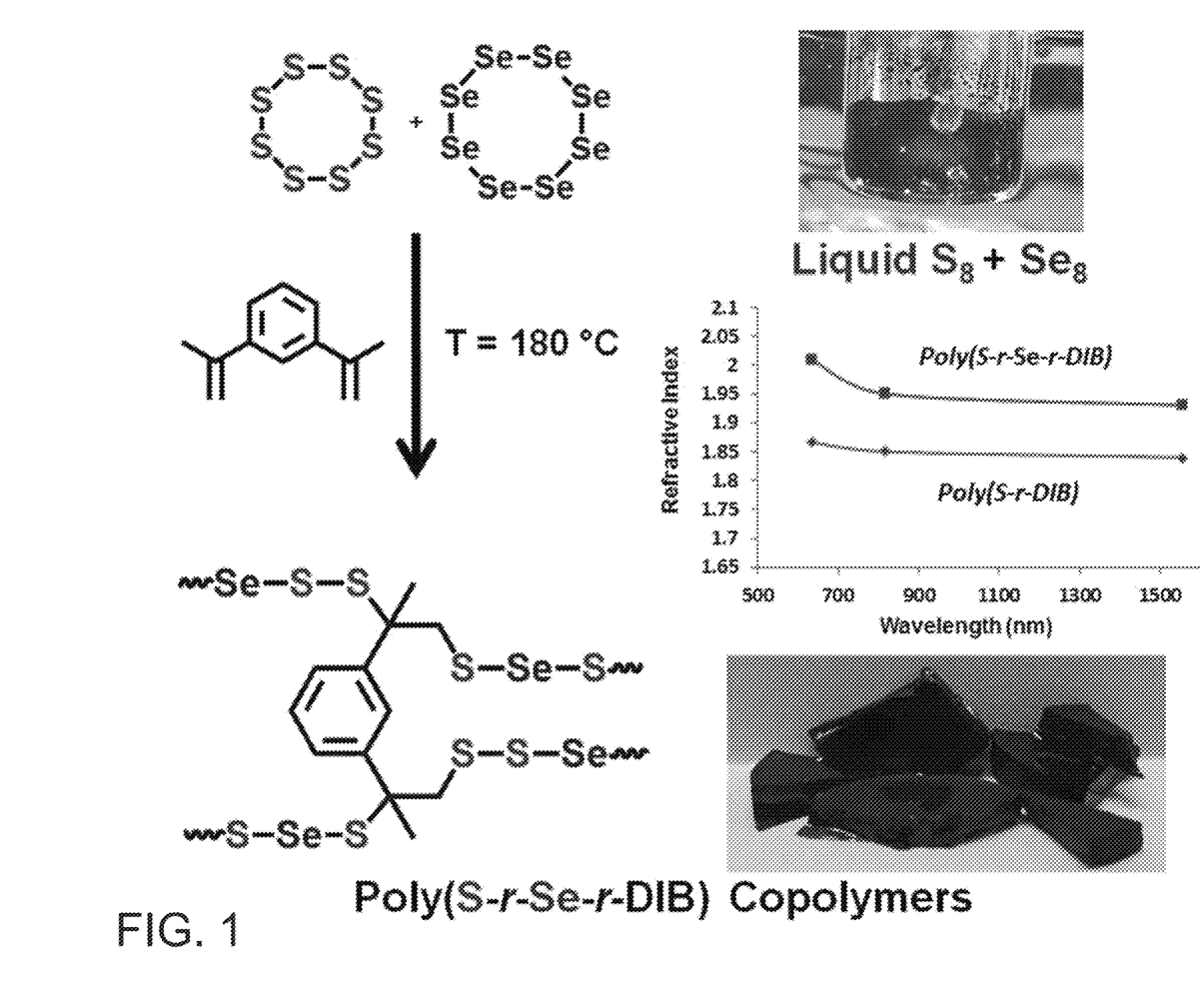
FIG. 1 shows an exemplary reaction schematic of elemental selenium and elemental sulfur polymerizing with comonomers to form chalcogenide-based copolymers with high Se and S content and high refractive index.
Figure 2:
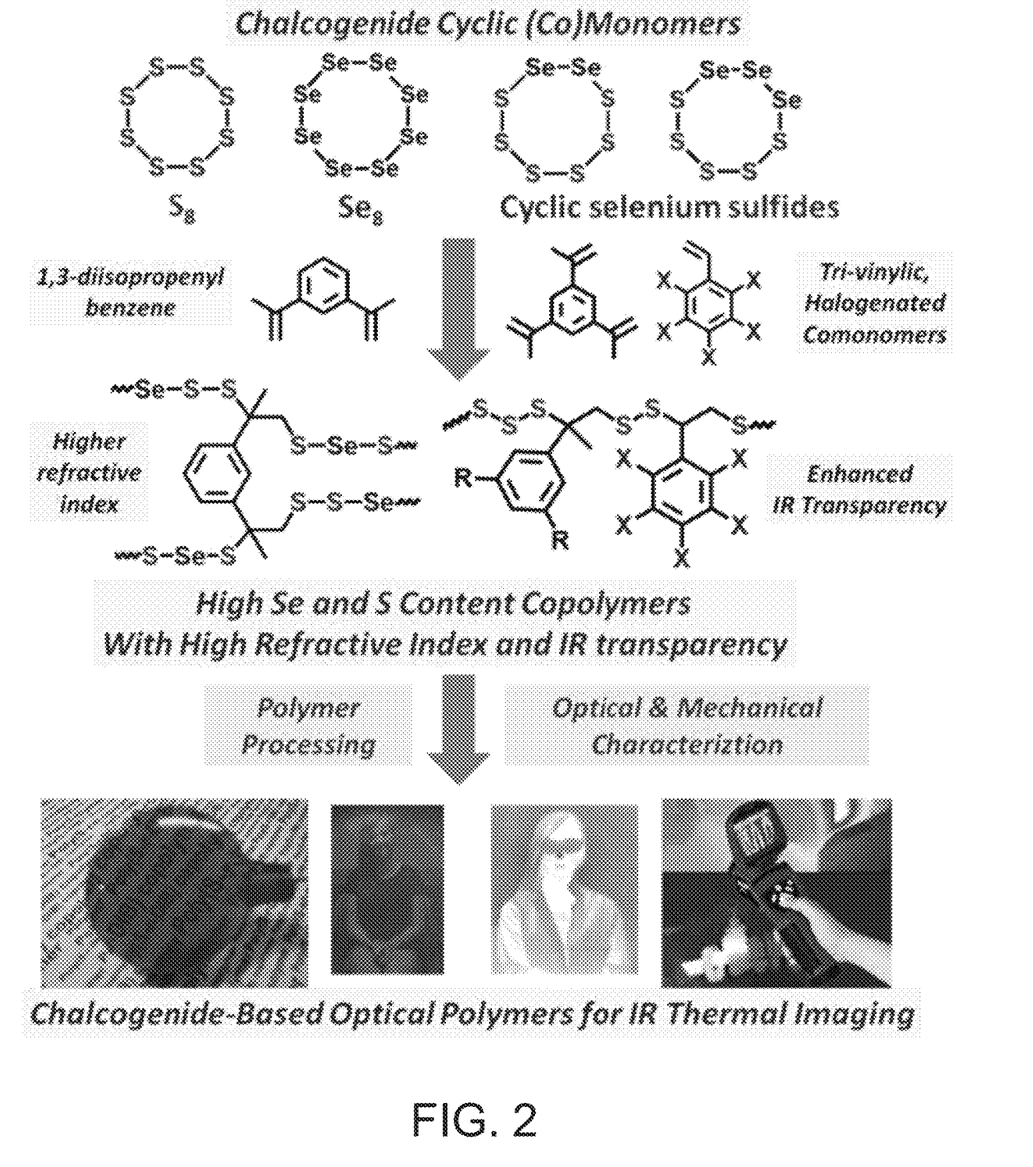
FIG. 2 shows an exemplary reaction schematic of elemental selenium or cyclic selenium sulfides, and elemental sulfur polymerizing with comonomers to form chalcogenide-based copolymers with high Se and S content. Further depicted are exemplary applications of said chalcogenic sulfur copolymers in IR thermal imaging.
Figure 3:
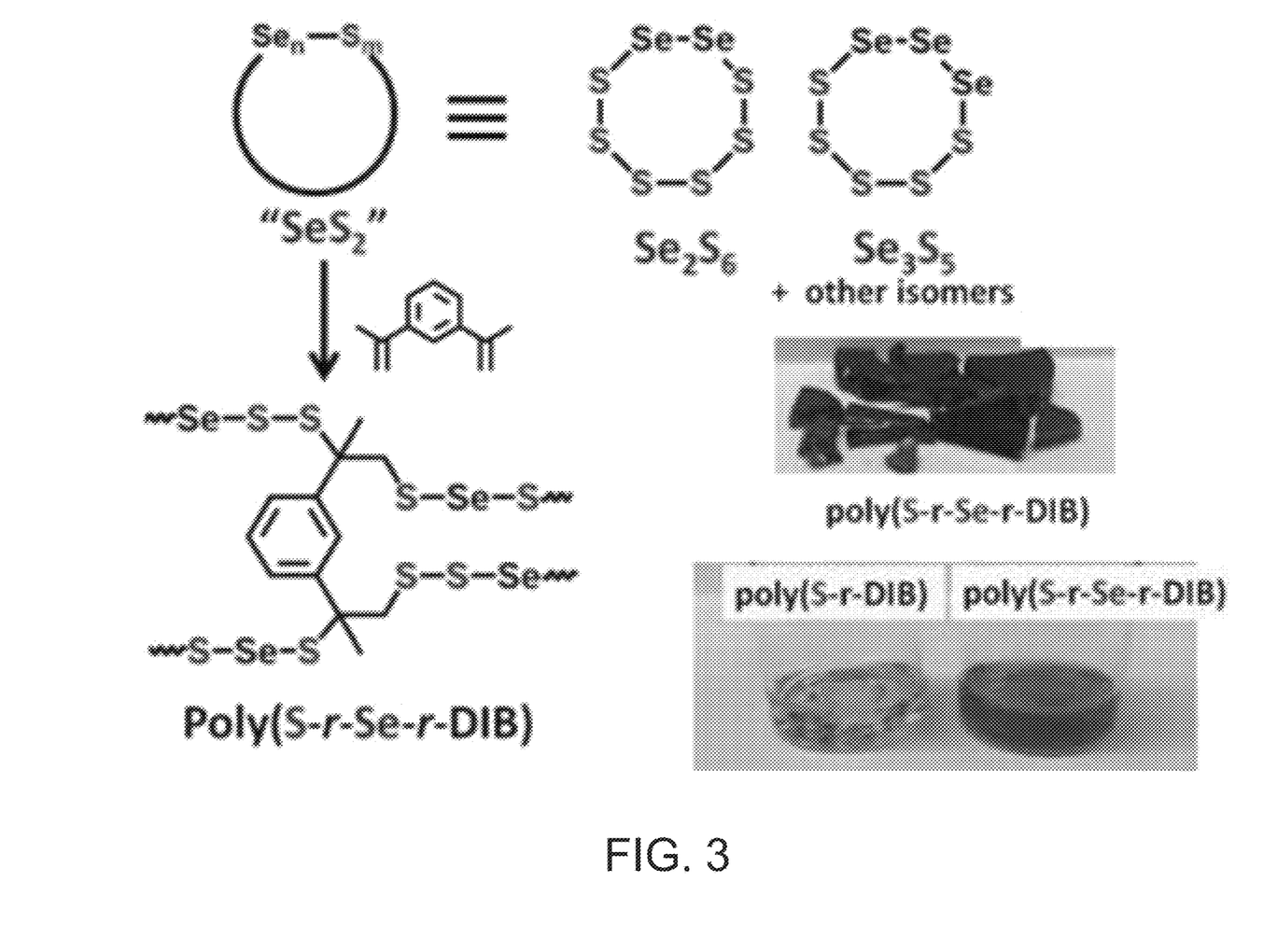
FIG. 3 shows an exemplary reaction schematic of cyclic selenium sulfides polymerizing with comonomers to form chalcogenide-based sulfur copolymers. In some embodiments, the cyclic selenium sulfides may comprise monomers according to the formula $Se_nS_m$, and isomers thereof. For example, the cyclic selenium sulfides may comprise mixtures of different isomers of $Se_2S_6$ and $Se_3S_5$.
Figure 4A:
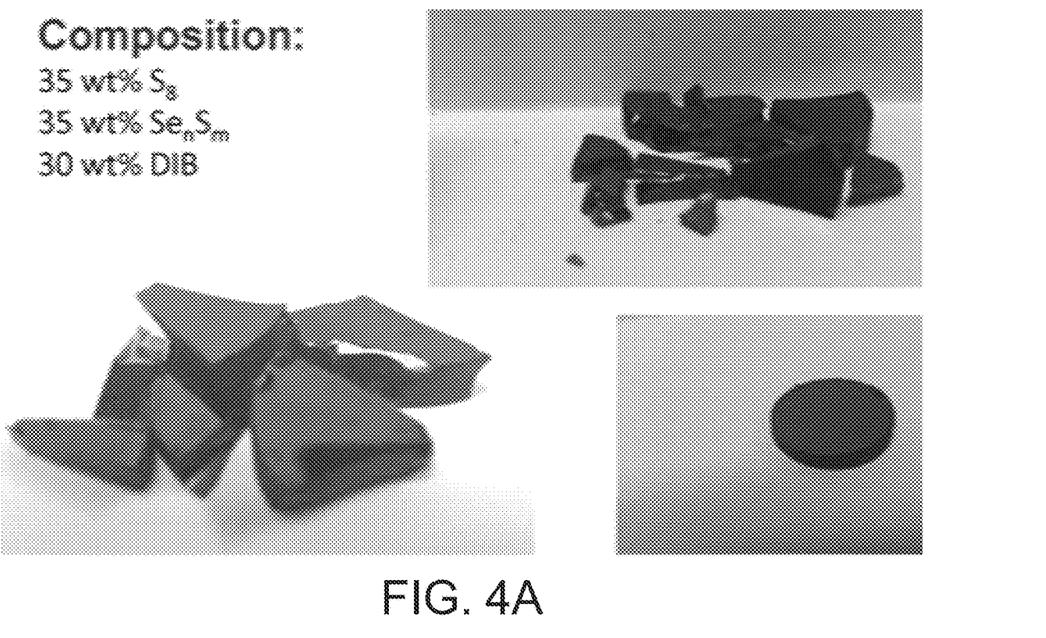
FIG. 4A shows an example of chalcogenide-based sulfur copolymer.
Figure 4B:
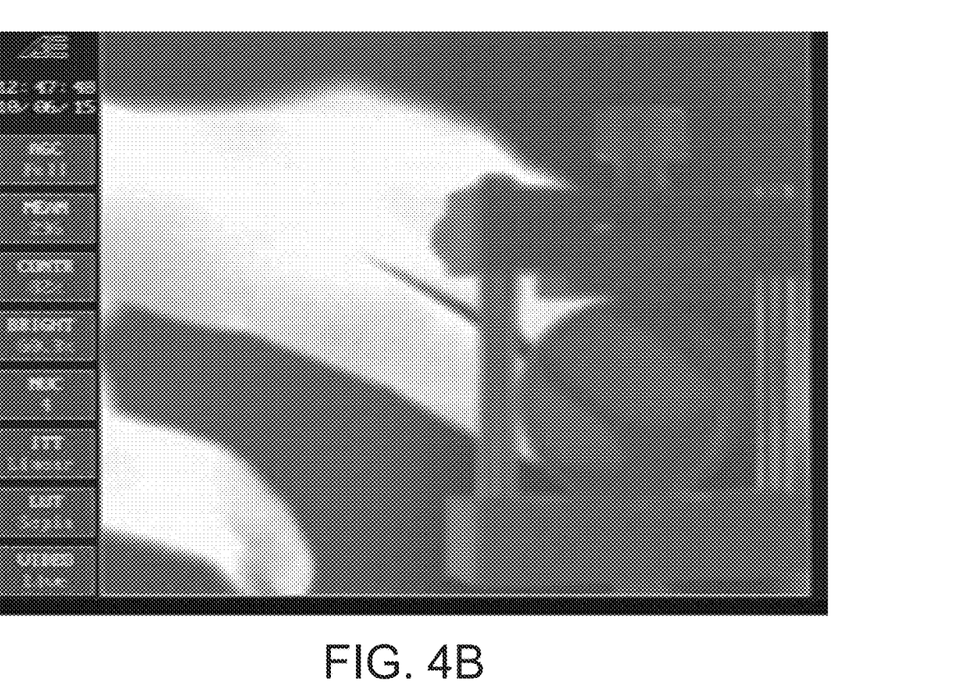
FIG. 4B depicts an IR imaging through an optical substrate containing a chalcogenide-based sulfur copolymer.
Figure 5:
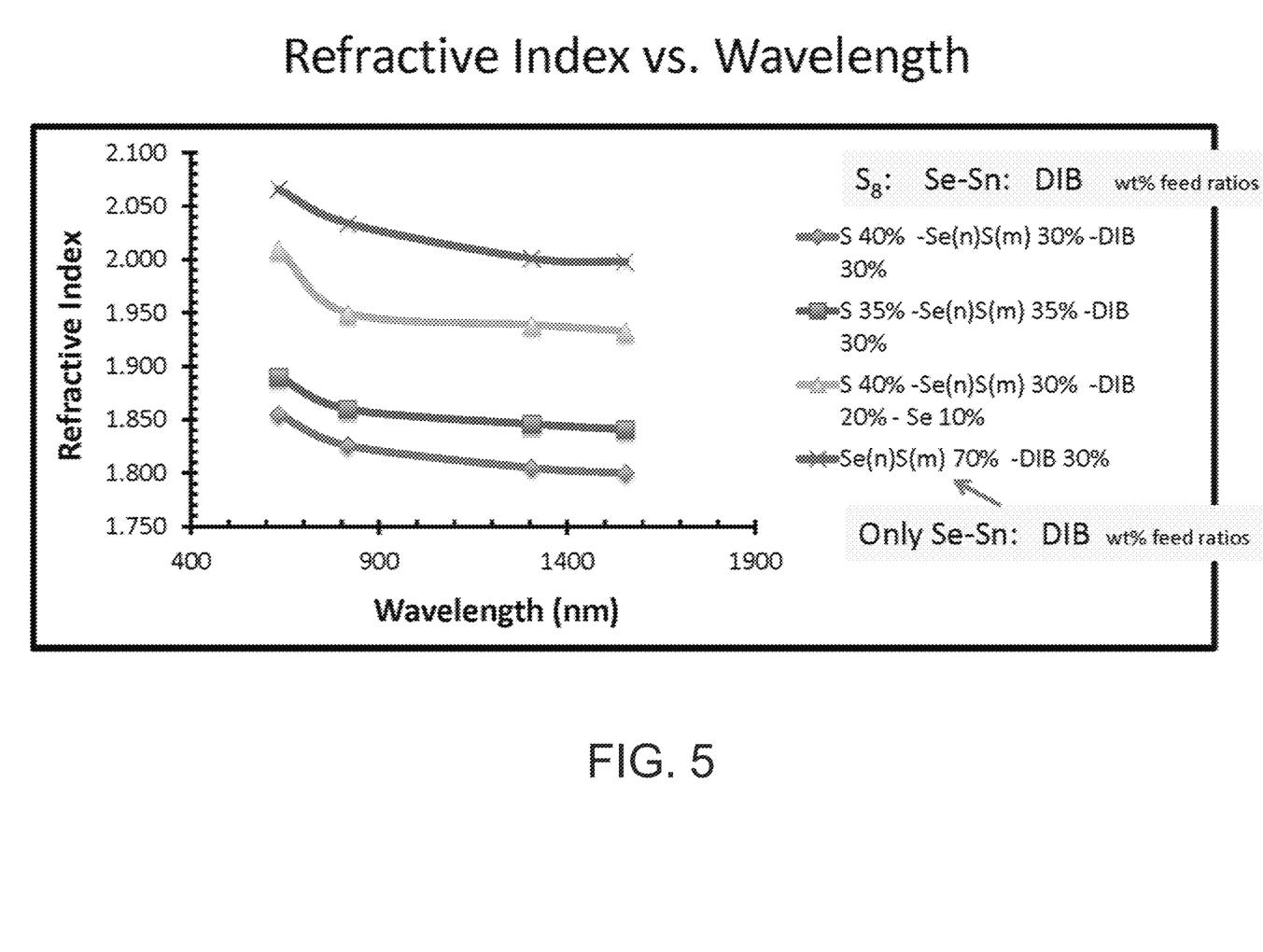
FIG. 5 shows a plot of refractive index vs. wavelength of chalcogenide-based sulfur copolymers having varying compositions.

Consistent with to FIG. 5, the following Table 1 shows the refractive indices of various compositions (in % wt) of the sulfur copolymer taken at different wavelengths. The varying compositions of the sulfur copolymer may be prepared according to the procedures outlined in Examples 1, 2, or 3.

Example 4

The following is a non-limiting example of a thermal reforming procedure of a self-healing optical substrate:
1. The optical substrate having a crack is placed in an oven.
2. The optical substrate is heated at about 100° C. for about 3 hrs.
3. The optical substrate is inspected to ensure that it is completely self-healed.

In some embodiments, any of the sulfur copolymers can be modified by reacting an available reactive functional group on the sulfur copolymer with a second comonomer to form a new copolymer material. The technique of reacting may be oxidative coupling, polymerization, or copolymerization.

Because both anionic and radical polymerization can occur in the polymerization reaction mixtures, any desirable combination of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, and acrylonitrile comonomers can be used in the same copolymer. As non-limiting examples, in one embodiment of the invention, the one or more monomers are a combination of one or more amine monomers and one or more styrenic monomers.

The person of skill in the art will select monomers and relative ratios thereof in order to provide the desired properties to the polymer. In certain embodiments, the one or more monomers include one or more polyfunctional monomers, optionally in combination with one or more monofunctional monomers. A polyfunctional monomer is one that includes more than one (e.g., 2, or 3) polymerizable amine, thiol, sulfide, alkynylly unsaturated, nitrone and/or nitroso, aldehyde, ketone, thiirane, ethylenically unsaturated, and/or epoxide moieties. Polyfunctional monomers can be used to cross-link selenium-sulfide or sulfur chains to adjust the properties of the polymer, as would be understood by the person of skill in the art. The multiple polymerizable groups of a polyfunctional monomer can be the same or different. For example, a polyfunctional monomer can be a polyvinyl monomer (e.g., divinyl, trivinyl), a polyisopropenyl monomer (e.g., diisoprenyl, triisoprenyl), a polyacryl monomer (e.g., diacryl, triacryl), a polymethacryl monomer (e.g., dimethacryl, trimethacryl), a polyunsaturated hydrocarbon monomer (e.g., diunsaturated, triunsaturated), a polyepoxide monomer (e.g., diepoxide, triepoxide), a polythiirane monomer (e.g., dithiirane, trithiirane), a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomers, a polynitrone mono-

TABLE 1

| Wavelength (nm) | S—$Se_nS_m$-DIB 40%-30%-30% | S—$Se_nS_m$-DIB 35%-35%-30% | S—$Se_nS_m$-DIB-Se 40%-30%-20%-10% | $Se_nS_m$-DIB 70%-30% |
|---|---|---|---|---|
| 632 | 1.855 | 1.890 | 2.010 | 2.066 |
| 816 | 1.826 | 1.860 | 1.950 | 2.034 |
| 1305 | 1.805 | 1.846 | 1.939 | 2.001 |
| 1554 | 1.800 | 1.841 | 1.933 | 1.998 | mers, a polyaldehyde monomers, a polyketone monomers, and a polyethylenically unsaturated monomers.

In other embodiments, the one or more polyfunctional can be a divinylbenzene, a diisopropenylbenzene, an alkylene di(meth)acrylate, a bisphenol A di(meth)acrylate, a terpene, a carotene, a divinyl (hetero)aromatic compound and a diisopropenyl (hetero)aromatic compound.

In some embodiments, the one or more polyfunctional monomers are at a level of about 2 to about 50 wt %, or about 2 to about 10 wt %, or about 10 to about 20 wt %, or about 20 to about 30 wt %, or about 30 to about 40 wt %, or about 40 to about 50 wt % of the sulfur copolymer. In some embodiments, the one or more monofunctional monomers are at a level up to about 5 wt %, or about 10 wt %, or about 15 wt % of the sulfur copolymer.

Fréchet-type benzyl ether dendrimers bearing styrenic terminal groups are miscible with liquid selenium-sulfide or sulfur and can be used as polyfunctional cross-linkers. In certain embodiments, the one or more polyfunctional monomers include one or more of a divinylbenzene, a diisopropenylbenzene, an alkylene di(meth)acrylate, a bisphenol A di(meth)acrylate, a terpene, a carotene, a divinyl (hetero) aromatic compound, and a diisopropenyl (hetero)aromatic compound. In other embodiments, a polyfunctional monomer can have one or more amine, thiol, sulfide, alkynylly unsaturated, nitrone and/or nitroso, aldehyde, ketone, thiirane, ethylenically unsaturated, and/or epoxide moieties moieties; and one or more amine, thiol, sulfide, alkynylly unsaturated, nitrone and/or nitroso, aldehyde, ketone, thiirane, ethylenically unsaturated, and/or epoxide moieties, wherein the first and second moieties are different. A non-limiting example is a divinylbenzene monoxide.

The sulfur copolymers can be made, for example, by polymerization of a molten mixture of selenium sulfide with the comonomers. Thus, in one aspect, the invention provides a method for making an optical sulfur copolymers as described above. The method includes heating a mixture of selenium sulfide and the one or more monomers together at a temperature sufficient to initiate polymerization (i.e., through free radical polymerization, through anionic polymerization, or through both, depending on the monomers used). Elemental sulfur or elemental selenium, or a combination thereof, may be added to the selenium sulfide prior to adding the comonomers. For example, in one embodiment, the method includes heating the mixture to a temperature in the range of about 120 ° C. to about 230° C., e.g., in the range of about 160° C. to about 230° C. The person of skill in the art will select conditions that provide the desired level of polymerization, In certain embodiments, the polymerization reaction is performed under ambient pressure. However, in other embodiments, the polymerization reaction can be performed at elevated pressure (e.g., in a bomb or an autoclave). Elevated pressures can be used to polymerize more volatile monomers, so that they do not vaporize under the elevated temperature reaction conditions.

In certain embodiments, it can be desirable to use a nucleophilic viscosity modifier in liquefying the cyclic selenium sulfide, for example, before adding one or more of the monomers (e.g., before adding any polyfunctional monomer). For example, in certain embodiments, the cyclic selenium sulfide is first heated with a viscosity modifier, then the viscosity-modified selenium sulfide is heated with one or more monomers (e.g., with one or more polyfunctional monomers). The nucleophilic viscosity modifier can be, for example, a phosphorus nucleophile (e.g., a phosphine), a sulfur nucleophile (e.g., a thiol) or an amine nucleophile (e.g., a primary or secondary amine). When cyclic selenium sulfide is heated in the absence of a nucleophilic viscosity modifier, the cyclic selenium sulfide rings can open to form, e.g., diradicals, which can combine to form linear polysulfide chains which can provide a relatively high overall viscosity to the molten material. Nucleophilic viscosity modifiers can break these linear chains into shorter lengths, thereby making shorter poly(selenium sulfides) that lower the overall viscosity of the molten material, making the cyclic selenium sulfide mixture easier to mix with and other species, and easier to stir for efficient processing. Some of the nucleophilic viscosity modifier will react to be retained as a covalently bound part of the copolymer, and some will react to form separate molecular species, with the relative amounts depending on nucleophile identity and reaction conditions. While some of the nucleophilic viscosity modifier may end up as a separate molecular species from the polymer chain, as used herein, nucleophilic viscosity modifiers may become part of the copolymer. Non-limiting examples of nucleophilic viscosity modifiers include triphenyl-phosphine, aniline, benzenethiol, and N,N-dimethylaminopyridine. Nucleophilic viscosity modifiers can be used, for example, in an amount up to about 10 wt %, or even up to about 5 wt % of the sulfur copolymer. When a nucleophilic viscosity modifier is used, in certain embodiments it can be used in the range of about 5 wt % to about 15 wt % of the sulfur copolymer.

In certain embodiments, a monofunctional monomer can be used to reduce the viscosity of the sulfur copolymer, for example, before adding other monomers (e.g., before adding any polyfunctional monomer). For example, in certain embodiments, the sulfur copolymer is first heated with one or more monofunctional monomers. While not intending to be bound by theory, the inventors surmise that inclusion of monofunctional monomers into the poly(selenium-sulfide) chains disrupts intermolecular associations of the selenium-sulfide and thus decreases the viscosity. The monofunctional monomer can be, for example, a mono(meth)acrylate such as benzyl methacrylate, a mono(oxirane) such as a styrene oxide or a glycidyl phenyl ether, or a mono(thiirane) such as t-butyl thiirane or phenoxymethylthiirane. A monofunctional monomer can be used to modify the viscosity of the sulfur copolymer, for example, in an amount up to about 10 wt %, up to about 5 wt %, or even up to about 2 wt % of the copolymer. When a monofunctional monomer can be used to modify the viscosity of the sulfur copolymer, in certain embodiments it can be used in the range of about 0.5 wt % to about 5 wt %, or even about 0.5 wt % to about 3 wt % of the sulfur copolymer.

Of course, viscosity modification is not required, so in other embodiments the cyclic selenium-sulfide is heated together with the one or more monomers (and particularly with one or more polyfunctional monomers) without viscosity modification. In other embodiments, a solvent, e.g., a halobenzene such as 1,2,4-trichlorobenzene, a benzyl ether, or a phenyl ether, can be used to modify the viscosity of the materials for ease of handling. The solvent can be added, for example, to the cyclic selenium-sulfide before reaction with a monomer in order to reduce its viscosity, or to the polymerized material in order to aid in processing into a desired form factor. For example, in one embodiment, a room temperature solution of any sulfur copolymer described herein (e.g., in prepolymeric form) may be used in a 3D printing process. A decrease in viscosity at elevated temperatures (e.g., >about 140° C.) can allow sufficient flow, for example, through the dispenser head of the 3D printer.

The polymers described herein can be partially cured to provide a more easily processable material, which can be processed into a desired form (e.g., into a desired shape, such as in the form of a free-standing shape or a device), then fully cured in a later operation. For example, the optical prepolymer can be formed, for example, by conversion of the one or more monomers at a level in the range of about 20 to about 50 mol %. For example, heating the sulfur copolymer to form the optical prepolymer can be performed for a time in the range of about 20 seconds to about five minutes, for example, at a temperature in the range of about 175° C. to about 195° C. In one embodiment, heating is performed for less than about 2 minutes at about 185° C. The person of skill in the art will determine the desired level of monomer conversion in the prepolymer stage to yield a processable prepolymer material, and will determine process conditions that can result in the desired level of monomer conversion.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed:

1. A method of producing a substrate using 3D printing, said method comprising:
   a. providing a print material comprising a sulfur copolymer, said sulfur copolymer formed from polymerization of:
      i. one or more chalcogenic monomers at a level of at least 50 wt % of the sulfur copolymer, wherein the chalcogenic monomers contain sulfur and selenium; and
      ii. one or more comonomers each selected from a group consisting of amine comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the sulfur copolymer;
   b. introducing said print material into a 3D printer; and
   c. dispensing said print material by successively applying layers of said print material to form the substrate;
   wherein the substrate produced from the print material has a refractive index of about 1.75-2.6 at a wavelength in a range of about 500 nm to about 8 μm.

2. The method of claim 1, wherein the chalcogenic monomers are cyclic selenium sulfide and isomers thereof or oligomers containing sulfur and selenium units.

3. The method of claim 2, wherein the oligomer containing sulfur and selenium units is derived from elemental sulfur and elemental selenium.

4. The method of claim 2, wherein the sulfur copolymer comprises at least about 30 wt % of sulfur.

5. The method of claim 3, wherein the sulfur copolymer comprises at least about 30 wt % of elemental selenium.

6. The method of claim 2, wherein the print material comprises at least about 30 wt % of sulfur, at least about 30 wt % of selenium, and about 15-25 wt % of the comonomers.

7. The method of claim 1, wherein the chalcogenic monomers are polymerized with the one or more comonomers via free radical polymerization, controlled radical polymerization, ring-opening polymerization, ring-opening metathesis polymerization, step-growth polymerization, or chain-growth polymerization.

8. The method of claim 1, wherein polymerizing the comonomers with the chalcogenic monomers enables at least one functional sulfur moiety of the chalcogenic monomers to bond with at least one functional moiety of the one or more monomers.

9. The method of claim 1, wherein the print material is in a form of a filament, liquid, gel, or powder.

10. The method of claim 1, further comprising dispensing a binding material to each layer of print material.

11. The method of claim 1, further comprising activating the print material via thermal, chemical, thermochemical, or photo/light activation, or infrared photo-heating or photo-patterning, thereby hardening the print material to form the substrate.

12. The method of claim 1, wherein the substrate produced from the print material is substantially transparent in an infrared or visible spectrum, wherein the transparent substrate is a film, a lens, or a free-standing object.

13. The method of claim 1, wherein the substrate is an optical device component configured for use as a transmitting material in an infrared imaging device, wherein the optical device component is a lens, a window, a microlens array, a waveguide, a Bragg reflector, or an optical fiber.

14. A method of producing a substrate using stereolithography, said method comprising:
   a. providing a liquid print material comprising a sulfur copolymer having photocurable moieties, said sulfur copolymer comprising:
      i. one or more chalcogenic monomers at a level of at least 50 wt % of the sulfur copolymer, wherein the chalcogenic monomers contain sulfur and selenium; and
      ii. one or more comonomers each selected from a group consisting of amine, comonomers, thiol comonomers, sulfide comonomers, alkynylly unsaturated comonomers, epoxide comonomers, nitrone comonomers, aldehyde comonomers, ketone comonomers, thiirane comonomers, ethylenically unsaturated comonomers, styrenic comonomers, vinylic comonomers, methacrylate comonomers, acrylonitrile comonomers, allylic monomers, acrylate monomers, vinylpyridine monomers, isobutylene monomers, maleimide monomers, norbornene monomers, monomers having at least one vinyl ether moiety, and monomers having at least one isopropenyl moiety, at a level in the range of about 5-50 wt % of the sulfur copolymer;

b. adding said liquid print material into a reservoir; and c. selectively photopolymerizing said print material in the reservoir to produce the substrate;

wherein the photocurable moieties enable photopolymerization of said print material, wherein the substrate produced from the print material has a refractive index of about 1.75-2.6 at a wavelength in a range of about 500 nm to about 8 μm.

15. The method of claim 14, wherein the chalcogenic monomers are cyclic selenium sulfide and isomers thereof or oligomers containing sulfur and selenium units.

16. The method of claim 15, wherein the oligomer containing sulfur and selenium units is derived from elemental sulfur and elemental selenium.

17. The method of claim 15, wherein the sulfur copolymer comprises at least about 30 wt % of sulfur.

18. The method of claim 16, wherein the sulfur copolymer comprises at least about 30 wt % of elemental selenium.

19. The method of claim 15, wherein the print material comprises at least about 30 wt % of sulfur, at least about 30 wt % of selenium, and about 15-25 wt % of the comonomers.

20. The method of claim 14, wherein the photocurable moieties of the sulfur copolymer are selected from a group consisting of vinyl, epoxide, azide, cinnamate, coumarin, benzophenone, and unsaturated moieties.

* * * * *